United States Patent
Lisziewicz et al.

(10) Patent No.: US 6,251,874 B1
(45) Date of Patent: *Jun. 26, 2001

(54) METHOD OF INHIBITING HUMAN IMMUNODEFICIENCY VIRUS USING HYDROXUREA AND A REVERSE TRANSCRIPTASE INHIBITOR IN VIVO

(75) Inventors: Julianna Lisziewicz; Franco Lori, both of Bethesda, MD (US)

(73) Assignee: Research Institute for Genetic and Human Therapy (R.I.G.H.T.)

( * ) Notice: Subject to any disclaimer, the term of this patent is extended or adjusted under 35 U.S.C. 154(b) by 0 days.

This patent is subject to a terminal disclaimer.

(21) Appl. No.: 09/048,886

(22) Filed: Mar. 26, 1998

(51) Int. Cl.$^7$ .................... A61K 31/07; A61K 31/17
(52) U.S. Cl. .................. 514/45; 514/50; 514/441; 514/579; 514/588

(58) Field of Search ............... 514/45, 588, 579, 514/50, 441

(56) References Cited

U.S. PATENT DOCUMENTS

| | | | | |
|---|---|---|---|---|
| 5,521,161 | * | 5/1996 | Malley et al. | 514/45 |
| 5,736,526 | * | 4/1998 | Malley et al. | 514/45 |
| 5,736,527 | * | 4/1998 | Malley et al. | 514/45 |
| 5,977,086 | * | 11/1999 | Lisziewicz et al. | 514/45 |

* cited by examiner

Primary Examiner—Gary Geist
Assistant Examiner—Howard Owens
(74) Attorney, Agent, or Firm—Valerie E. Looper (57) ABSTRACT

A method for treating HIV infection in human beings comprising the step of measuring viremia, and if viremia is less than 50,000–100,00 copies per milliliter, administering a combination of compounds selected from the group consisting of hydroxyurea, and one or more reverse transcriptase inhibitors.

2 Claims, 6 Drawing Sheets

METHOD OF INHIBITING HUMAN IMMUNODEFICIENCY VIRUS USING HYDROXUREA AND A REVERSE TRANSCRIPTASE INHIBITOR IN VIVO

FIELD OF THE INVENTION

The present invention relates generally to the field of treatment of human beings with reverse transcriptase dependent viruses such as Human Immunodeficiency Virus (HIV) infections. The inventors have found that the combination of hydroxyurea (HU) and a reverse transcriptase inhibitor without a protease inhibitor can reduce the level in the blood to non-detectability (less than 500 copies per milliliter) and can also be used for long-term therapy (years) in human beings without provoking viral rebound, even in cases where patients have developed genotypic resistance to the reverse transcriptase inhibitor. This combination is relatively inexpensive, well-tolerated, and forgiving of irregularities in the medication regimen.

BACKGROUND OF THE INVENTION

The inventors had previously disclosed the first known case where a patient who had been HIV positive stopped treatment without immediate rebound of the viral population in the blood. In U.S. Ser. No. 08/812,515, filed Mar. 7, 1997, Method of Inhibiting Human Immunodeficiency Virus by combined use of Hydroxyurea, a nucleoside analog, and a protease inhibitor, which is incorporated by reference as if set forth in full, it was disclosed that a triple drug combination including hydroxyurea, a reverse transcriptase inhibitor, and a protease inhibitor, can drive the virus to undetectable levels in both the blood, and more significantly, the lymph nodes, according to the most sensitive tests then available. At the time, it was supposed that the triple combination derived much of its potency from the protease inhibitor.

As recently as a year ago, drug cocktails which did not use hydroxyurea such as a triple drug combination involving the use of AZT, 3TC and protease inhibitors had been suggested for the treatment of HIV-1 infection and eradication of the virus. The efficacy of this combination was thought to originate from the potency of the protease inhibitors and the mechanism of action of the AZT/3TC combination in inhibiting the rebound of resistant mutants. And indeed, many patients experienced impressive drops in viral load in the bloodstream, so that virus was undetectable, with virus becoming undetectable for some patients in as little as eight to sixteen weeks. Viral load, measured as HIV-1 RNA is the best available indicator of disease progression and reduced concentration of HIV-1 in various tissues and fluids in response to antiretroviral therapy, and is predictive of improved prognosis (Mellors, J. W. et al. Science 272(5265) 1167–1170, 1996). Viral load in the blood is more conveniently determined than viral load in other tissues.

Despite their promise, protease inhibitors are new drugs which must be explored in detail before they are marketed. As a result, they are expensive enough to be impractical for many patients. Most protease inhibitors must be taken on a very exacting schedule, or they will lose their effect. The drugs do not always elicit a patient response (defined as a significant drop in plasma viral load). Neither the protease inhibitors nor 3TC easily penetrate to certain organs such as lymph nodes and the brain, and the combination of protease inhibitor, AZT and 3TC apparently does not completely eradicate HIV-1 in macrophages or in quiescent cells, which are major reservoirs of HIV-1. Further, patients who have interrupted therapy using AZT, 3TC and protease inhibitors and then rebounded cannot be as effectively treated with either the same combination or the same combination with another protease inhibitor because they develop resistant mutants. Many times the resistance to one protease inhibitor extends to others. There currently exists a pool of patients who, having used a protease inhibitor in the past, can no longer benefit from the newer protease inhibitors. Finally, the protease inhibitor-containing combinations without hydroxyurea have shown at best, response rates of 80–90% and 53% "failure"—a combined figure including people who never responded to therapy, those who could not tolerate side effects, those who responded initially but later saw a return of detectable virus, and those who had difficulty adhering to the strict dosing regimens required by the drugs. See Project Inform Perspective 23:1–3, November 1997.

One explanation for the eventual rebound of viral load after apparently successful treatment may be found in Identification of a Reservoir for HIV-1 in Patients on Highly Active Retroviral Therapy, Finzi, et al., Science Magazine 278 (5341):1295. In a study of 22 patients successfully treated with highly active anti-retroviral therapy for up to 30 months, a highly aggressive new test method found replication-competent virus was routinely recovered from resting CD4+ T lymphocytes. The frequency of resting CD4+T cells harboring latent HIV-1 was low, 0.2 to 16.4 per million cells, and in cross-sectional analysis, did not decrease with increasing time in therapy.

Hyroxyurea has been widely used over the last three decades for the treatment of leukemia, sickle cell anemia, and has more recently been suggested for use in the treatment of HIV infections. EPO patent publication 94918016.0 filed May 17, 1994 and corresponding to U.S. Ser. No. 08/065,814, filed May 21, 1993, which is incorporated herein as if set forth in full, describes the in vitro data suggesting that it would be worthwhile to try administration of hydroxyurea in combination with ddl in human volunteers. The data shows that hydroxyurea used alone had an antiviral effect, and that ddl was the more potent of the two when each were used alone in vitro. When the combination was tried in human beings, a therapeutic effect was observed in that the viral load in the blood, or plasma viremia, was reduced, although the amount of virus in the blood never went below the threshhold level of detection. In one study Jessen et al. JAMA 277:18 1437–8 1997, hydroxyurea and ddl were used in combination for up to 65 weeks, but the patients did not reach an undetectable level (defined as less than 500 copies per ml).

In a later study, a therapeutic effect was again found, but the amount of virus in the blood failed to reach 100 copies per milliliter, the threshhold level of detection for the test used in that study. See Lori et al Combination of a Drug Targeting the Cell with a Drug Targeting the Virus Controls Human Immunodeficiency Virus Type 1 Resistance, AIDS Research and Human Retroviruses vol. 13, Number 16, Mary Ann Liebert, Inc. (1997) Further, patients who were treated with both hydroxyurea and the reverse transcriptase inhibitor ddl had higher rates of formation of ddl resistant mutations than those treated with ddl alone, although the overall level of virus remained low and rather constant. An incident was reported where two individuals on hydroxyurea and ddl treatment for a year stopped treatment for a year, without rebound. However, the initial level of viral load for each of them was so low that others have doubted whether these individuals had an infection.

The inventors have now found that hydroxyurea in combination with a reverse transcriptase inhibitor alone can be used to reduce the level of viral load in the blood to undetectable levels (less than 500 copies per milliliter), and that such treatment can be sustained without rebound over long periods of time. This discovery yields an important tool, particularly for use in treating patients for whom treatment with protease inhibitors is impractical, but also in a generalized scheme of treatment for the disease.

BRIEF DESCRIPTION OF THE DRAWINGS

FIGS. 1 and 1A compare the response of patients to ddl alone and ddl plus hydroxyurea.

FIGS. 4 and 4A compare the response of patients to combinations of ddl, d4T and a placebo with ddl, d4T, and hydroxyurea. FIG. 4A shows CD4 cell count over time. A change occurs at the 12 week mark where patients "nonresponsive" to the placebo combination replaced the placebo with hydroxyurea.

DETAILED DESCRIPTION OF THE INVENTION

Hydroxyurea is one of many inhibitors of ribonucleotide reductase, an enzyme known for catalyzing the reduction of ribonucleoside diphosphates to their deoxyribonucleoside counterparts for DNA synthesis. In the present invention, hydroxyurea inhibits viral replication, and also acts to down-modulate the immune system. Another material which inhibits viral replication and down-modulates the immune system is cyclosporine, a cyclophilin inhibitor. Other ribonucleotide reductase inhibitors include guanazole, 3,4-dihydroxybenzo-hydroxamic acid, N,3,4,5-tetrahydroxybenzimidamide HCl, 3,4-dihydroxybenzamidoxime HCl, 5-hydroxy-2-formylpyridine thiosemicarbazones, and α-(N)-heterocyclic carboxaldehyde thiosemicarbazones, 4-methyl-5-amino-1-formylisoquinoline thiosemicarbazone, N-hydroxy-N'-amino-guanidine (HAG) derivatives, 5-methyl-4-aminoisoquinoline thiosemicarbazone, diaziquone, doxorubicin, 2,3-dihydroxylbenzoyl-dipeptides and 3,4-dihydroxylbenzoyl-dipeptides, iron-complexed 2-acetylpyridine 5-[(2-chloroanilino)-thiocarbonyl]-thiocarbonohydrazone (348U87), iron-complexed 2-acetylpyridine-5-[(dimethylamino)thiocarbonyl]-thiocarbonohydrazone (A1110U), 2'-deoxy-2'-methylenecytidine 5'-diphosphate (MdCDP) and 2'-deoxy-2', 2'-difluorocytidine 5'-diphospahte (dFdCDP), 2-chloro-9-(2-deoxy-2-fluoro-B-D-arabinofuranosyl)-adenosine (Cl-F-ara-A), diethyldithiocarbamate (DDC), 2,2'-bipyridyl-6-carbothioamide, phosphonylmethyl ethers of acyclic nucleoside analogs, [eg. diphosphates of N-(S)-(3-hydroxy-2-phosphonylmethoxypropyl and N-2-phosphonylmethoxyethyl) derivatives of purine and pyrimidine bases], nitrosourea compounds, acylclonucleoside hydroxamic acids (e.g., N-hydroxy-a-(2-hydroxyethoxy)-1 (2H)-pyrimidineacetamides 1-3, and 2-acetylpyridine 4-(2-morpholinoethyl)thio-semicarbazone(A723U)).

Hydroxyurea has been widely used in cancer therapy as a broad spectrum antineoplastic drug (R. C. Donehower, *Seminars in Oncology* 19 (Suppl. 9), 11 (1992)). Hydroxyurea is readily absorbed after oral ingestion, rapidly distributed in the body fluids, including the cerebrospinal fluid, and enters cells efficiently by passive diffusion (Id.). Its toxic effects are less profound and easier to control than other chemotherapeutic drugs (Id.).

In human chemotherapy, hydroxyurea is currently administered using two basic schedules: (a) a continuous daily oral dose of 20–40 mg per kg per day, or (b) an intermittent dose of 80 mg per kg per every third day. Either schedule could be used in the treatment of viral infections. Given the present invention, lower dosages of hydroxyurea may also be effective in treating HIV infections.

The presently preferred dosage range for use of hydroxyurea in treating HIV infections is 800–1500 mg per day, which can be divided over a 24 hour period, for example as 300–500 mg three times a day (TID), assuming an adult weighing about 70 kg. When the patient's weight is over 60 kg, 400 mg TID is preferred, for those under 60 kg, 300 mg TID is preferred. Hydroxyurea is classified as a mildly toxic drug and does not cause immunodepression. Myelotoxicity is hydroxyurea's dose-dependent toxicity. However, such toxicity can be easily monitored and it is constantly and rapidly reversible after decreasing the dose or suspending the treatment (Donehower, R. C., *Semin. Oncol.* 19:11 (1992). By monitoring simple parameters such as neutrofils, platelets and red blood cell counts, hydroxyurea can be administered for years, and sometimes for decades.

A second member of the combination of the present invention is a reverse transcriptase inhibitor. Examples include nucleoside analogs, such as the 2',3'-dideoxyinosine (ddl)(available as Videx@ from Bristol Myers-Squibb) used in the Examples. Nucleoside analogs are a class of compoounds known to inhibit HIV, and ddl is one of a handful of agents that have received formal approval in the United States for clinical use in the treatment of AIDS. See Clinical Microbiology Reviews, Supra, p. 200. Like zidovudine (3'-azido-2',3'-dideoxythymidine or azidothymidine [AZT] available from Glaxo Wellcome), zalcitabine (2',3'-dideoxycytidine [ddC](available as Hivid® from Hoffman-La Roche), lamivudine (2'-deoxy-3'-thiacytidine [3TC] available as Epivir® from Glaxo Wellcome) and stavudine (2',3'-didehydro-2',3'-dideoxythimidine [D4T] (available as Zerit® from Bristol Myers-Squibb), ddl belongs to the class of compounds known as 2',3'-dideoxynucleoside analogs, which, with some exceptions such as 2',3'-dideoxyuridine [DDU], are known to inhibit HIV replication, but have not been reported to clear any individual of the virus. Other nucleoside reverse transcriptase inhibitors include adefovir (Preveon® an adenine nucleotide analog from Gilead Sciences), and abacavir (1592U89 available from Glaxo Wellcome) and lubocavir (a guanosine analog available from Bristol Myers-Squibb). Non-nucleoside reverse transcription inhibitors include nevirapine (Viramune™ available from Boehringer Ingelheim Pharmaceuticals, Inc.), delaviridine (Rescriptor® available from Pharmacia & Upjohn) and efavirenz (available as Sustiva®, from DuPont Merck)

Currently, antiviral therapy requires doses of ddl at 200 mg BID or 400 mg once (QID) per day for an adult human. Similar dosages may be used in the present invention. However, use of the combination drugs may increase the effectiveness of these nucleoside phosphate analogs so that they can be used at lower dosages or less frequently. In combination with hydroxyurea, the presently preferred range for ddl is 100–300 mg twice a day (BID), assuming an adult weighing 70 kg. When d4T is used with either hydroxyurea or a combination of hydroxyurea and ddl, the preferred amount is at least about 40 mg BID.

The inventors have found that, in certain cases, the same result achieved by triple and quadruple drug combinations including protease inhibitors can be achieved without using the protease inhibitor, and employing instead a combination of hydroxyurea and one or more reverse transcriptase inhibitors. The present invention also includes a method of analyzing whether the protease inhibitors are required, and selecting a treatment regimen. Thus this invention includes a course of treatment that, at one time or another, may include the use of one or more protease inhibitors.

Of the potential protease inhibitors, compounds such as hydroxyethylamine derivatives, hydroxyethylene derivatives, (hydroxyethyl)urea derivatives, norstantine derivatives, symmetric dihydroxyethylene derivatives, and other dihydroxyethylene derivatives have been suggested, along with protease inhibitors containing the dihydroxyethylene transition state isostere and its derivatives having various novel and high-affinity ligands at the $P_2$ position, including 3-tetrahydrofuran and pyran urethanes, cyclic sulfolanes and tetrahydrofuranylglucines, as well as the $P_3$ position, including pyrazine amides. In addition, constrained "reduced amide"-type inhibitors have been constructed in which three amino acid residues of the polypeptide chain were locked into a γ-turn conformation and designated γ-turn mimetics. Other alternatives include penicillin-derived compounds, non-peptide cyclic ureas. At present, the inventors have no basis for distinguishing among the many potential protease inhibitors that may be used in combination with HU and a reverse transcriptase inhibitor.

The protease inhibitors used in the present invention include Indinavir sulfate, (available as Crixivan™ capsules from Merck & Co., Inc, West Point, Pa.) saquinavir (Invirase® and Fortovase® available from Hoffman-LaRouche), ritonavir (Norvir® available from Abott Laboratories), ABT-378 (Abott Laboratories) and nelfinavir (Viracept® available from Agouron Pharmaceuticals), and amprenavir, formerly GW141 (available from Glaxo WellcomeNertex).

In addition to reverse transcriptase inhibitors and protease inhibitors, the present invention may utilise integrase inhibitors such as AR177 (Zintenvir® available from Aronex); fusion inhibitors such as pentafuside, (T-20) and cytokine inhibitors such as (AOP)-Rantes.

Suitable human dosages for these compounds can vary widely. However, such dosages can readily be determined by those of skill in the art. For example, dosages to adult humans of from about 0.1 mg to about 1 g or even 10 g are contemplated.

As disclosed in U.S. Ser. No. 08/812,515, the combination of compounds of the present invention may be administered by any conventional route, and the particular dosage, toxicity, and mechanism for delivery of the individual of drugs of the present invention are either already known, or can be readily determined by conventional empirical techniques, as can dosages for the combinations. The use of combinations may result in the ability to use lower amounts of one or more of the constituents. One of ordinary skill in the art will recognize that different dosages and intervals may be appropriate.

The present invention is based on the recognition that there are multiple sources of new viral particles being produced during the course of the disease, that different drug combinations may used to control them, and that the amount of virus in the blood can be used as an indicator of which type of combination is most advantageously used.

Where very high viral loads in the blood indicate that certain types of activated T-cells are producing large amounts of viral particles, a combination including a protease inhibitor is indicated. Such a combination may also advantageously include hydroxyurea and one or more reverse transcriptase inhibitors, integrase inhibitors, fusion inhibitors and cytokine inhibitors. Particularly preferred are the reverse transcriptase inhibitors including AZT, 3TC, ddC, ddI, d4T, abacavir, adefovir, nevirapine, delviridine, efavirenz, and mixtures thereof. Of these, ddI and d4T and mixtures thereof are most preferred.

Where viral loads in the blood are lower, the activated cells are producing less virus, and the role of the quiescent cell begins to predominate. Then a combination targeting cells such as quiescent lymphocytes and macrophages is indicated. Generally, where the level of virus in the blood is about 50,000 copies per mL or less, combinations including hydroxyurea and one or more reverse transcriptase inhibitors are preferred. This is especially true if CD4 counts are conserved. Particularly preferred are the reverse transcriptase inhibitors including AZT, 3TC, ddC, ddI, d4T, abacavir, adefovir, nevirapine, delviridine, efavirenz, and mixtures thereof. Of these, ddI and d4T and mixtures thereof are most preferred.

The drug combinations using hydroxyurea but not a protease inhibitor of the present invention may be used before and after acute infection, before seroconversion, and after seroconversion, as well as before and after various other types of treatment, so long as the plasma viral load is no more than about 50,000–100,000 copies per mL. Further, the hyroxyurea-containing combinations (without protease inhibitors) might be administered prophylactically to high-risk individuals without raising concerns about the viability of protease inhibitor therapy for that individual in the future. Where viral load is more than about 20,000 copies per milliliter, is preferred that the treatment be continued for at least about twelve to fifteen months. Depending on the status of the patient, the time of the treatment can be from several months to lifelong.

The present invention also contemplates the possibility of deliberately activating certain types of quiescent cells during combination therapy. As disclosed in U.S. Ser. No. 09/048,576, activation of the immune system during treatment can be used to reduce the viral population harbored by quiescent cells, and may provide a therapeutic advantage. The cells could be activated by vaccination against any of a number of diseases known to activate such cells, including, for example, HIV-1, Hepatitis B, Influenza, and Polio vaccination. HIV-1 genetic immunization is preferred, as disclosed in U.S. Ser. No. 60/604,627, filed Feb. 21, 1996. Such activation should preferably take place after the elimination of active virus production (that is, after the patient's viral load is undetectable (defined as less than about 200 copies per mL) for at least 2 months). Repeated activation would be helpful to ensure that all quiescent cells harboring HIV-1 DNA had been activated.

SUMMARY OF THE INVENTION

It is an object of the present invention to provide a method of inhibiting the replication of retroviruses such as HIV-1, HIV-2, HTLV-1 and HTLV-2 and other reverse-transcriptase-dependent viruses such as Hepatitis B virus in human cells. A further object of this invention is to provide a course of treatment for HIV infections that reduces the presence of the virus in both plasma and the lymphoid system, and which inhibits viral rebound after cessation of treatment. It is yet a further object of this invention to provide a method of treating HIV infection which includes an indication of the type of drug combination most advantageously used under different circumstances. Yet another object of this invention is to provide a treatment for HIV which relatively less expensive and has relatively low toxicity, therefore increasing its suitability for widespread use in a large population.

The present inventors have found that, where indicated, the combination of hydroxyurea (HU) and one or more reverse transcriptase inhibitors such as 2',3'-dideoxyinosine (ddI) and 2',3'-didehydro-2'3'-dideoxythimidine (d4T) may be used to achieve the same end result as the protease inhibitor combinations without hydroxyurea. These modes of treatment, in addition to the use of combinations including hydroxyurea, protease inhibitors, reverse transcriptase inhibitors, and other immunizatiion techniques, can be combined to yield an method of treatment that is more effective, and minimizes both expense and toxicity to the individual.

These and other objects and advantages of the present invention will become apparent through the text and examples herein.

The following Examples are presented for the purpose of illustrating the practice of the present invention. They do not limit the invention, or the claims which follow.

EXAMPLE 1

Figure 1:
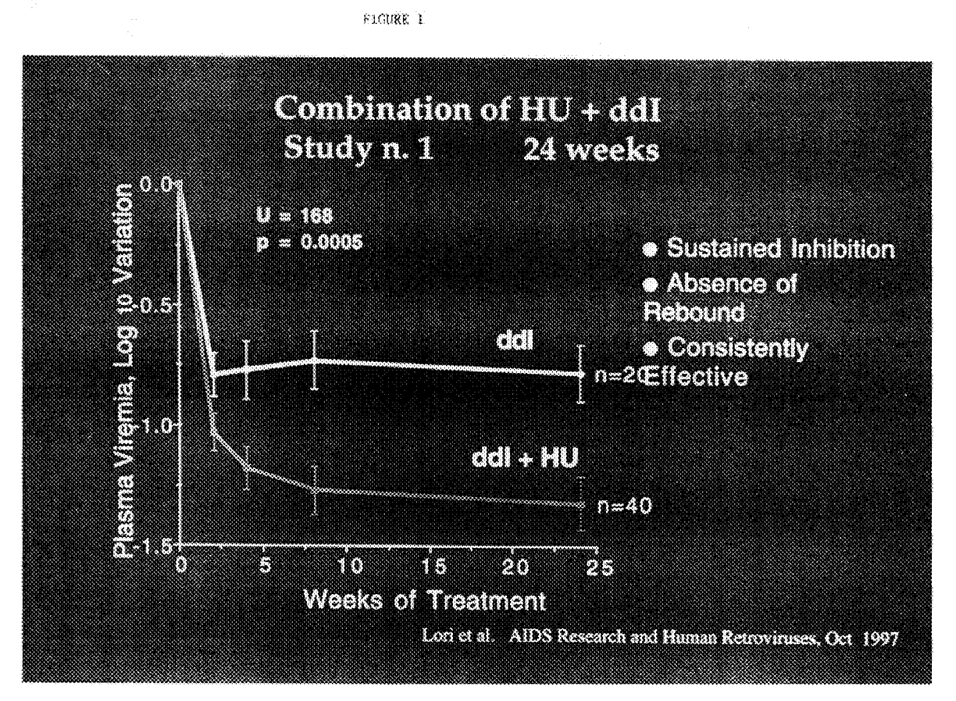
FIG. 1 shows virus levels in the blood over time.
Figure 1A:
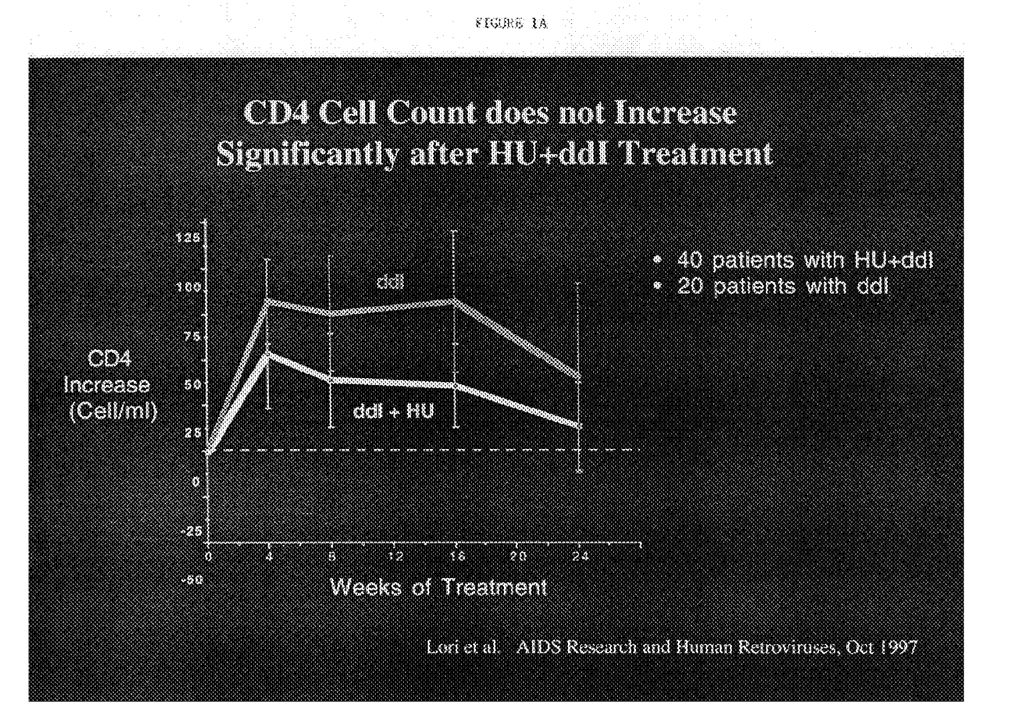
FIG. 1A shows CD4 cell counts over the same time frame.
Figure 2:
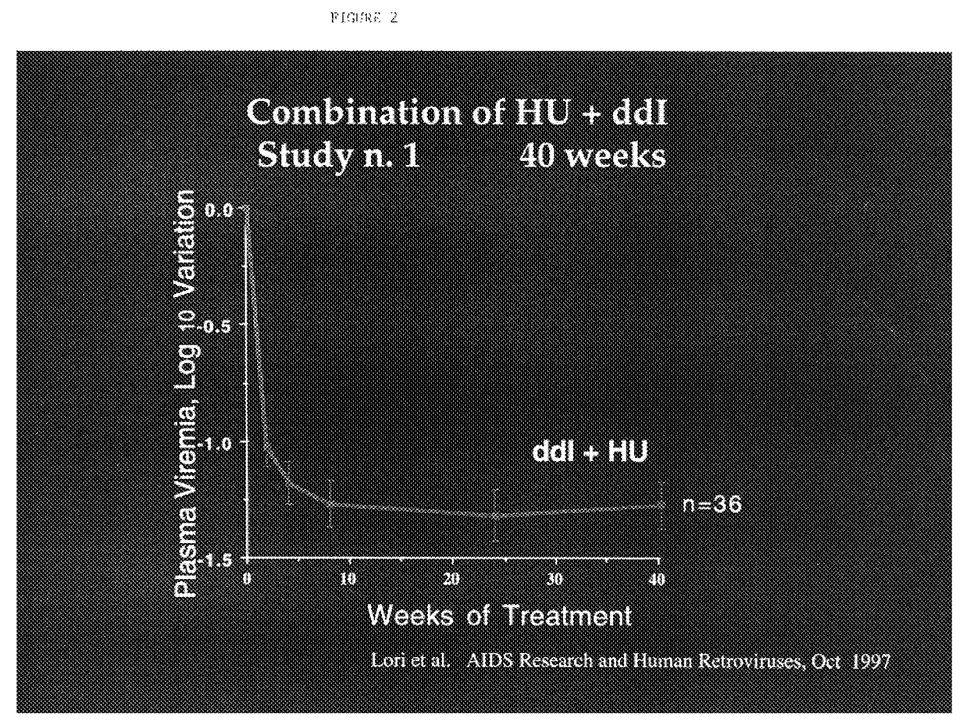
FIG. 2 is a curve describing data derived for thirty-six patients for a 40 week study using HU and ddl therapy.
Figure 3:
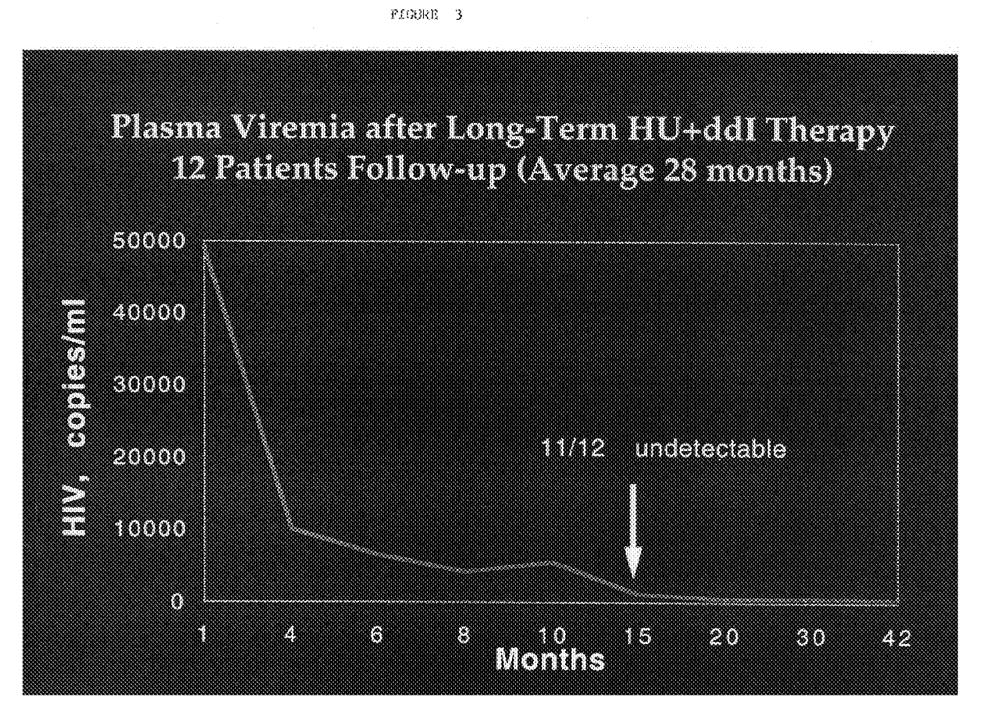
FIG. 3 is a curve describing data derived from a follow-up on 12 patients, for an average of 28 months using HU and ddl therapy.
Figure 4:
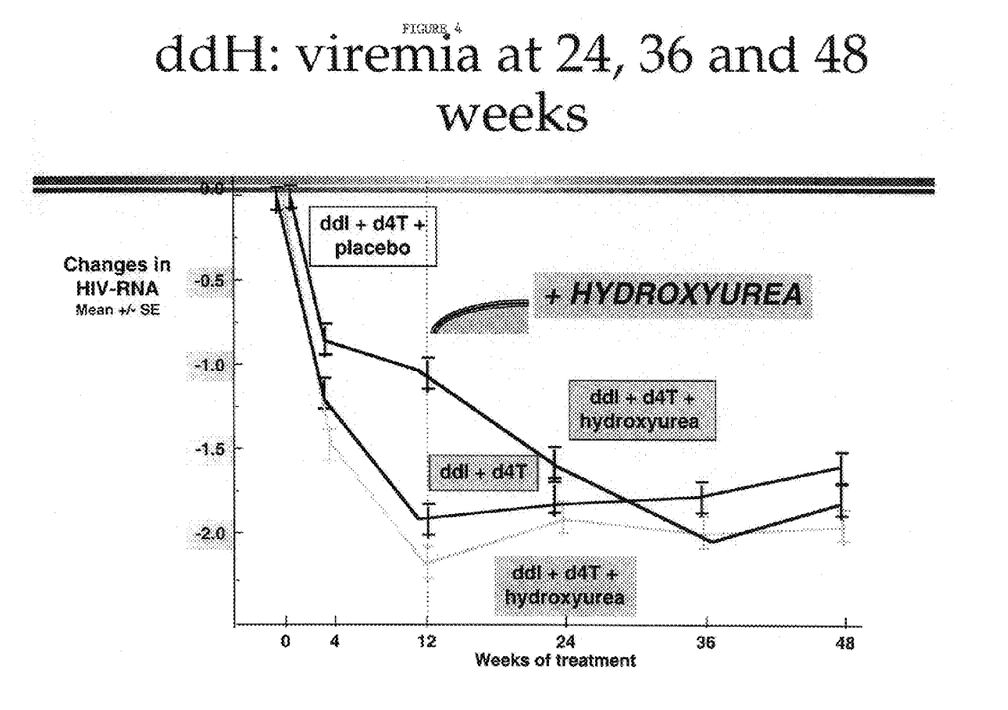
FIG. 4 shows virus levels in the blood over time.
Figure 4A:
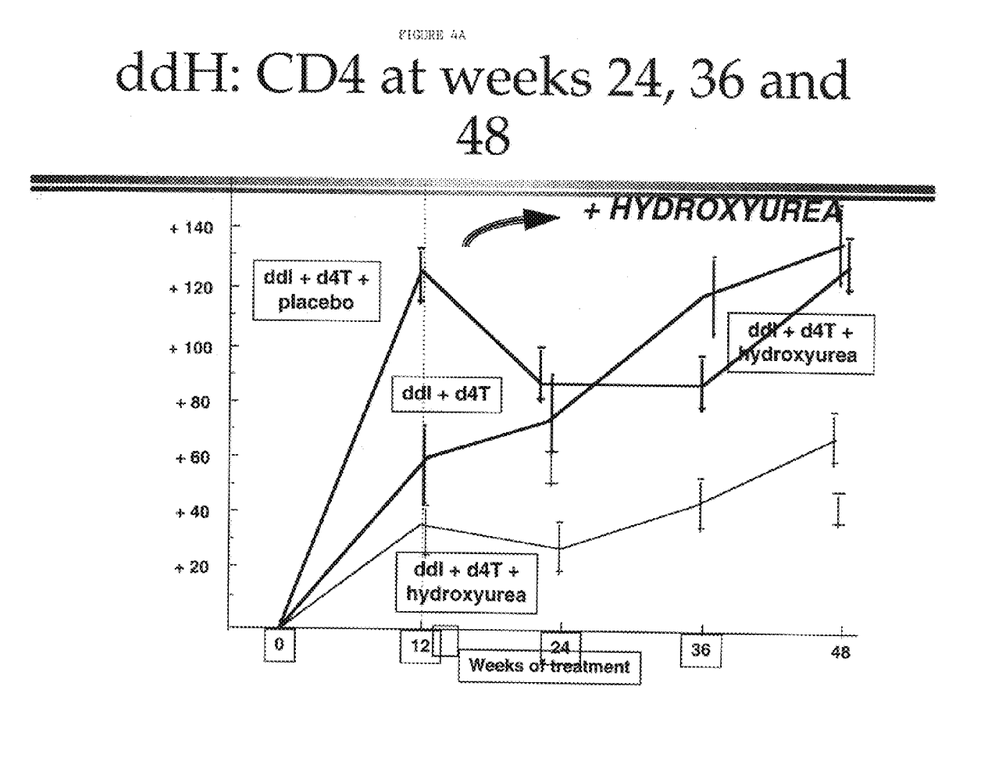

Sixty HIV-infected subjects, who were asymptomatic and had about 250 to 500 CD4 cells per $\mu l$ (a normal cell count) and who may have had previous treatment, but not with ddI, were divided into two groups. Group 1 had twenty patients with a dosage of 200 mg ddI twice daily. Group 2 had forty patients with a dosage of 200 mg ddI twice daily plus 500 mg hydroxyurea twice daily. The study duration was twenty-four weeks, with a possible extension to 48 weeks. FIG. 1 shows the results for the two populations as variation in plasma viremia over time. The combination of ddI plus hydroxyurea worked better than ddI alone, although a slow downward trend was noticeable, virus was still detectable in the patients blood. In addition, the CD4 cell counts for those treated with the double combination were lower than those receiving only ddI. This raised some cause for concern, as HIV-1 infection typically causes a decline in both the numbers of CD4 cells and their effectiveness. See FIG. 1A.

EXAMPLE 2

The study continued with thirty-six patients on the combination of ddI and hydroxyurea. After forty weeks, the curve was either flat or beginning a slow rise.

EXAMPLE 3

After 42 months all of the 12 follow-up patients had undetectable (less than 200 copies per milliliter) virus in the blood. Eleven out of twelve had reached undetectable status by about fifteen months. None had rebounded. The shape of the curve is not inconsistent with the hypothesis that a second source of viral particles predominated after about ten months.

EXAMPLE 4

In another study, the combinations of hydroxyurea plus ddI and ddI plus d4T were compared. One group received 40 mg d4T twice daily, 200 mg ddI twice daily, and 500 mg hydroxyurea twice daily. The second group received 40 mg d4T twice daily, 200 mg ddI twice daily, and a placebo. At twelve weeks, 54% of the group receiving the hydroxyurea combination had fewer than 200 copies of virus per mL, compared to the placebo group. Those with less than 200 copies were then subjected to a more sensitive test, and 19% of the hydroxyurea group had less than twenty copies of virus per mL, while the placebo group had 8% with less than 20 copies of virus per mL. Non-responders 25 (defined as those with more than 200 copies of virus per mL were present in both groups: the hydroxyurea group had 40% and the placebo group had 71 %. At twelve weeks, the code of randomization was opened and patients were subsequently treated according to virological response. Thus, a number of patients formerly treated with a placebo were started on hydroxyurea as well, yielding a triple combination of ddI, d4T and hydroxyurea. All combinations showed a drop in virus levels, with the population possibly beginning to rise by the 48th week. Addition of hydroxyurea to the control group decreased virus level in the blood, and also decreased and then increased CD4 cell counts.

EXAMPLE 5

Six individuals were treated with the combination of hydroxyurea, a nucleoside analog, and a protease inhibitor. The general course of treatment was HU, 5–8 mg/kg TID; ddI, 200 mg BID, Indinavir 800mg/TID. Four of them were treated within 4–7 weeks following primary infection and before seroconversion, that is, when the Western Blot was not completely positive.

Three patients were treated from <1 year to >5 years after seroconversion. In all the individuals the levels of plasma viremia became undetectable within 3–25 weeks after treatment. All the data is shown below in Tables 1–6, each of which is further identified by a two-letter code.

Three individuals began treatment within 14 to 31 days following the onset of symptoms (DFOS) of a primary HIV-1 infection and before seroconversion. In all of these individuals, the levels of plasma viremia became undetectable within 73 to 136 DFOS (with a drop of viremia between 2.7 to 3.4 logs) and remained undetectable during the course of treatment. None of these patients fully seroconverted, despite a documented exposure to HIV-1 ranging between 163 and 236 days. Their Western Blot patterns remained almost unaltered during the course of the observation. See Tables 1–3, for results of BM, FC, and SH. Moreover, a significant, sharp increase of the CD4/CD8 ratio and CD4 count was observed in all three patients. Lymph nodes were collected from these patients at different time points to detect HIV-1 RNA by in situ hybridization. In most cases over 40 million cells were sampled, and HIV-1 RNA was detected in only one patient (FC).

The first node of FC was analyzed 8 weeks after beginning treatment, while the virus was still detectable in the plasma, and HIV-1 RNA was mainly associated to the follicular dendritic cells. At this time, the CD4 count and CD4/CD8 ratio was normal. Later, when HIV-1 was no longer detectable in the plasma, another inguinal lymph node was obtained and analyzed as before. No HIV-1 RNA was detected at that time. Again, DNA was extracted from the half of the lymph node which was frozen and tested by PCR analysis using 2 different primers and also a nested primer (sensitivity of this test is to one copy of viral DNA per sample). The PCR was positive, indicating that FC had at least one copy of HIV-1 DNA in the lymph node. See Table 1.

In patient SH, HIV-1 became undetectable in the plasma at 105 days after treatment had begun, with a decrease in viremia of 3.2 log from the baseline. The CD4 counts and CD4/CD8 ratios increased promptly after treatment began (from 0.33 to 0.95 in 33 days). In two consecutive analyses, no RNA was detected in the lymph nodes, but at least 1 copy of viral DNA was detected at 176 days from the onset of symptoms and 145 days from the start of treatment. No significant changes were observed in the Western blot profile of SH during the course of the follow-up. See Table 2.

The third patient (BM, see Table 3) was treated starting 7 weeks after the probable date of infection. Between 19 and 22 days after starting the therapy, he interrupted the treatment for three days, concomitantly with an episode of orchitis. A rebound of plasma viremia was monitored immediately after the three day suspension. Therapy was started again, and at about week 5 after initiating treatment, HIV-1 was undetectable in the plasma. At week 16, an inguinal lymph node was analyzed and 2 RNA producing cells were found out of 44 million cells screened. At week 17, treatment was again interrupted, this time due to an episode of acute hepatitis A. Despite the massive immune stimulation due to this concomitant viral infection, this individual did not show any sign of viral rebound during the following two weeks, although a positive value was found but could not be confirmed. The same week, BM again started taking the therapy. After an additional 4–5 weeks of therapy taken at irregular intervals, the patient discontinued treatment altogether. Another lymph node was obtained 18 days following final suspension of therapy, and 2 RNA producing cells were found out of a total of 44 million cells screened. No DNA could be detected in this lymph node, even after repeated nested PCR analysis. The plasma tested positive for RNA 40 days after treatment suspension at very low levels, but this positivity could not be confirmed. During all the course of the follow-up, cell counts did not significantly change, and the Western blot profile remained practically unchanged.

Semen of patients FC, SH and BM was tested at 141, 176, and 214 days from onset of symptoms, respectively, and HIV-1 RNA was undetectable by NASBA (sensitivity<400 copies/ml). Similarly, the semen of the other patients, when tested, showed negative results.

The viral load variations in the plasma and the changes in the CD4 and CD8 absolute/relative counts of the three patients who were treated after seroconversion did not differ significantly from those who were treated before seroconversion. Patients TD and LF showed sharp increases in CD4 counts back to normal levels and their CD4/CD8 ratios now range between 1.1 and 1.4. See Tables 4 and 5. The one patient who had the longest (>5 years) infection before therapy and started with the lowest CD4 count (330), LJ, showed marked improvement also, but progress was slower. This patient became virus negative in the plasma only after 25 weeks of treatment, and the increase of the CD4/CD8 ratio was slower and less significant than in the other individuals. The CD4/CD8 ratio remains at about 0.4 at this time. See Table 6.

The patient who had been seropositive for the longest period of time, LJ, (See Table 7) had low but detectable levels of HIV-1 RNA and proteins in the lymph node after 27 weeks of treatment.

Patient TD had been seroconverted for approximately 6 months before treatment had begun. Patient TD currently shows no traces of viral DNA or RNA in the sperm, serum, or lymph nodes. This patient has had a history of hepatitis infection in March, 1996.

These data indicate that the combination of hydroxyurea, ddl and a protease inhibitor present a potent new combination that can rapidly clear the virus from plasma and lymph nodes, and inhibit viral rebound after cessation of treatment. Further, this combination blocks HIV-1 replication in the lymphoid system and, at least in one case, shows hope for HIV-1 eradication.

In addition, these data indicate that HIV-1 infection is treatable as an emergency disease. Patients should be tested not for seroconversion, but for free virus particles in the blood if there are any symptoms or suspicion of infection, and treated immediately with the combination therapy before seroconversion takes place. The present invention will eliminate the free virus, block new infections, restore the immune system, and may eliminate virus integration in millions of cells. This method would also be economical, as treatment would be begun earlier and be of shorter duration than treatment for people with chronic infections. The present results show that the patients treated early restored the normal lymphocyte status in short periods of time (see CD4+cells and CD4/CD8 ratio). However, the patient that had been infected for 5–9 years (U, see Table 6) could not as rapidly restore the lymphocyte status even after 9 months of therapy, even though virus production was completely blocked. This demonstrates that the in vivo clearance rate cannot be generalized for all treatments that apparently reduce the presence of virus in plasma.

Further, the same patient, unlike the patients with fresh infections, did not demonstrate restoration of the T-cell repertoire (CD4 counts and CD4/CD8 ratios) to the normal levels. This result indicates that late in the infections, T-cells do not turn over at the same rate as they did earlier, and regeneration of T-cells may be impaired. It further suggests early treatment.

The present results also indicate that a method of eliminating quiescent cells, that is, cells which have integrated viral DNA, but do not currently express the genes or produce virus. HIV-1 DNA was measured in the lymphocytes of the patients with a highly sensitive nested PCR able to detect as little as 1 copy of viral DNA. Two patients in this group had no detectable HIV-1 DNA in the lymphoid organ and 3 had detectable DNA. Other investigators have also reported (in all cases) detectable DNA in the lymphoid organs even in the absence of virus producing cells (Markovitz, Retrovirus Conference, 1997) The present inventors are not aware of any other patients other than the two in the present study (TD, BM) who have undetectable viral DNA in the lymphoid organs. The only common feature of these patients is that both experienced hepatitis infection. BM had Hepatitis A and TD had hepatitis B. Both infections are characterized by activation of cells which can harbor HIV-1 DNA. After activation, these cells can produce viral particles which will be mainly defective in the presence of protease inhibitors. HU and ddl will work at the early phase, inhibiting reverse transcription with two different mechanisms, consequently blocking both new infection and new DNA integration.

The present results also show that early treatment of individuals (BM, SH, FC and TD, LF) infected by HIV-1 led to a profound modification of the natural evolution of HIV-1 infection.

First, HIV-1 became and remained undetectable in the plasma. The implication of this result is highly relevant. In fact, only 8% of individuals with less than 4,350 copies of RNA per milliliter of blood plasma soon after infection developed AIDS 5 years after infection, whereas 62% of those with values greater than 36,270 progressed to AIDS (Mellors, J. W. et al., Science 272(5265) 1167–1170, 1996). In the ACTG 175 study, a decrease of 1.0 log in the concentration of HIV-1 RNA from the baseline after therapy with nucleoside analogues in patients with CD4 counts between 200 and 500 per cubic millimeter was associated significantly with a 65% reduction in the risk of AIDS or death (N.Engl. J. Med. 1996 Oct 10:335(15):1091–8). All the patients analyzed here had high levels of viral replication (between 89,390 and 487,955 copies/mL) before the treatment and this load was decreased between 2.7 and 3.4 logs, that is, below 200 copies/mL.

Second, also in the lymph node compartment, which has been described as the major reservoir of the virus, only traces of HIV-1 RNA and/or DNA could be inconstantly detected. In particular, follicular dendritic cell-associated HIV-1 found in patient FC 57 days following treatment rapidly disappeared 70 days later, indicating the rapid clearance of follicular dendritic cell-associated HIV-1 following this therapy.

Third, CD4 counts increased promptly to normal levels and CD4/CD8 ratios were normalized in patients LF, TD, FC, SH, BM, whereas these values typically fail to increase to normal.

Fourth, lack of a full seroconversion in 3 of these patients treated prior to seroconversion suggests that the replication of the virus has at least been reduced to a minimum. Of particular interest is the observation that all of the above considerations hold true even after the treatment has been suspended in one of the patients. Despite a possible smoldering expression of viral RNA, DNA was repeatedly undetectable in the lymph nodes, even with a methodology able to detect a single copy of viral DNA.

Fifth, we have recently shown on an animal model (unpublished) that an early treatment with ddl and ddl with hydroxyurea, although unable to prevent the infection of pigtail macaques by a lethal dose of SIV, reduced the viral load and rescued the animals from death. This also demonstrates that early, effective treatment can completely change the course of lentivirus infection.

The combination of hydroxyurea, 2',3'-dideoxyinosine (ddl)eoxyinosine and Indinavir during the acute primary phase of infection resulted in a very potent, long lasting block of HIV-1 replication in the blood, lymph nodes and semen and in the restoration of the immune system. In one patient, the treatment was suspended without substantial viral rebound or seroconversion.

While particular embodiments of the invention have been described in detail, it will be apparent to those skilled in the art that these embodiments are exemplary rather than limiting, and the true scope of the invention is that defined by the claims that follow.

TABLE 1

VIRAL LOAD, LYMPHOCYTE AND SEROCONVERSION ANALYSES FOR PATIENT FC

Infected: End July beginning of August according to Heiko
3 day break in therapy: Sept 15–18, 1996

Therapy begun 2 Sept. 96
HU 400 mg TID
ddI 200 mg BID
INDINAVIR 800 mg TID

| VIRAL LOAD IN THE BLOOD | | | | VIRAL LOAD IN THE LYMPH NODE | | | | | |
|---|---|---|---|---|---|---|---|---|---|
| D/M/Y | bDNA/PCR | PCR/RIGHT | | D/M/Y p24 antigen expression | | HIV-RNA in situ | | HIV DNA PCR | VIRAL LOAD SEMEN |
| 23.8.96 | 800,000 | | | 29.10.96 | | | | | 07.01.97 |
| 26.8.96 | 1,280,000 | | | FDC | Cells | FDC | Cells | | <400 copies/ml |
| 2.9.96 | 785,000 | 487955 | start 2–9 | – | – | + | (few) + | Not detected | |
| 9.9.96 | 37,000 | 22497 | stop 15–18 | 07.01.97 | | | | | |
| 20.9.96 | 21,000 | 13929 | | | | | | | |
| 27.9.96 | 500 | 5919 | | – | – | – | – | positive | |
| 29.10.96 | 500 | 673 | | | | | | | |
| 18.11.96 | 400 | <200 | | | | | | | |
| 23.12.96 | 400 | <200 | | | | | | | |
| 6.1.97 | | <200 | | | | | | | |
| 14.01.97 | 500 | | | | | | | | |
| 29.1.97 | | <200 | | | | | | | |

| LYMPHOCYTE POPULATION ANALYSIS | | | | | | | | |
|---|---|---|---|---|---|---|---|---|
| D/M/Y | Lymph. | B.Ly | T-Ly | CD4 | CD4 % | CD8 | CD8 % | Ratio |
| 26.10.96 | 2,543 | 200 | 2,010 | 1,220 | 48 | 970 | 38 | 1.26 |
| 18.8.96 | 1,336 | 110 | 900 | 380 | 28 | 680 | 51 | 0.56 |
| 23.8.96 | 1,548 | 80 | 1,020 | 330 | 21 | 850 | 55 | 0.39 |
| 27.8.96 | 1,974 | 99 | 1,210 | 474 | 24 | 1,046 | 53 | 0.45 |
| 2.9.96 | 3,256 | 130 | 2,583 | 684 | 21 | 2,084 | 64 | 0.33 |
| 9.9.96 | 2,415 | 242 | 1,771 | 652 | 27 | 1,232 | 51 | 0.53 |
| 20.9.96 | 1,546 | 216 | 1,199 | 680 | 44 | 526 | 34 | 1.29 |
| 18.11.96 | 2,149 | 279 | 1,624 | 946 | 44 | 688 | 32 | 1.38 |
| 06.01.97 | 1,480 | 252 | 1,139 | 696 | 47 | 459 | 31 | 1.52 |
| 29.01.98 | 2,416 | 314 | 1,705 | 821 | 34 | 870 | 36 | 0.94 |

TABLE 1-continued

VIRAL LOAD, LYMPHOCYTE AND SEROCONVERSION ANALYSES FOR PATIENT FC

SEROCONVERSION BY WESTERN BLOT TEST

| Date | HIV 1 + 2 | gp160 | gp120 | p65 | p55 | gp41/43 | p32 | p24 | p18 |
|---|---|---|---|---|---|---|---|---|---|
| 19.08.96 | ± | ± | − | − | − | − | − | ± | − |
| 23.08.96 | ± | + | ± | − | − | − | − | ± | ± |
| 02.09.96 | ± | + | ± | − | − | − | − | + | + |
| 09.09.96 | + | + | ± | − | − | − | − | ± | ± |
| 27.09.96 | + | + | ± | ± | − | − | − | + | + |
| 23.12.96 | + | + | ± | ± | ± | ± | ± | ± | ± |

TABLE 2

VIRAL LOAD, LYMPHOCYTE AND SEROCONVERSION ANALYSIS OF PATIENT SH

Infection: The patient says he was infected June 96  
He went to hospital 15 July 96 with high fever Therapy begun 27 July, 96  
HU 400 mg TID  
ddI 200 mg BID  
INDINAVIR 800 mg TID

| VIRAL LOAD IN THE BLOOD | | | VIRAL LOAD IN THE LYMPH NODE D/M/Y | | | | | |
|---|---|---|---|---|---|---|---|---|
| D/M/Y | bDNA/PCR | PCR/RIGHT | p24 antigen expression | | HIV-RNA in situ | | HIV DNA PCR | VIRAL LOAD SEMEN |
| 19.7.96 | 199000 | | 16.10.96 | | | | | 07.01.97 |
| 22.7.96 | 192000 | 319146 | FDC | Cells | FDC | Cells | | <400 copies/ml |
| 26.7.96 | 3260000? | 871602 | − | − | − | − | Not detected | |
| 31.7.96 | 82310 | 143435 | 07.01.97 | | | | | |
| 20.8.96 | | 3100 | − | − | − | − | positive | |
| 23.9.96 | 500 | 918 | | | | | | |
| 25.10.96 | 500 | 266 | | | | | | |
| 28.11.96 | 500 | <200 | | | | | | |
| 12.12.96 | | <200 | | | | | | |
| 08.01.97 | 500 | | | | | | | |
| 29.1.97 | | <200 | | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 19.7.96 | 1,578 | 170 | 1,250 | 520 | 33 | 870 | 55 | 0.60 |
| 26.7.96 | 1,778 | 120 | 1,400 | 410 | 23 | 1,190 | 67 | 0.34 |
| 2.8.96 | 2,040 | 220 | 1,570 | 590 | 29 | 1,140 | 56 | 0.52 |
| 20.8.96 | 1,911 | 230 | 1,450 | 590 | 31 | 1,010 | 53 | 0.58 |
| 17.9.96 | 2,012 | 302 | 1,549 | 804 | 40 | 845 | 42 | 0.95 |
| 25.10.96 | 1,816 | 182 | 1,412 | 672 | 37 | 708 | 39 | 0.95 |
| 12.12.96 | 1,742 | 244 | 1,352 | 645 | 37 | 627 | 36 | 1.03 |
| 14.01.97 | 2,424 | 267 | 1,798 | 776 | 32 | 970 | 40 | 0.80 |
| 29.01.97 | 2,133 | 299 | 1,527 | 661 | 31 | 832 | 39 | 0.79 |

SEROCONVERSION BY WESTERN BLOT TEST

| D/M/Y | HIV 1 + 2 | gp160 | gp120 | p65 | p55 | gp41/43 | p32 | p24 | p18 |
|---|---|---|---|---|---|---|---|---|---|
| 19.07.96 | ± | ± | − | − | − | − | − | − | − |
| 02.08.96 | ± | ± | − | − | − | − | − | ± | − |
| 20.09.96 | ± | ± | − | − | − | − | − | ± | − |
| 17.09.96 | + | + | ± | − | − | − | − | ± | − |
| 04.10.96 | + | + | ± | − | − | − | − | ± | − |
| 12.12.96 | + | + | ± | − | − | − | − | ± | ± |

TABLE 3

VIRAL LOAD, LYMPHOCYTE AND SEROCONVERSION ANALYSES FOR PATIENT BM

Infection 10 May 96  
Testis infection 10 July 96; stop therapy: 12–19 July 1996  
Acute hepatitis A infection: stop therapy 26 Oct. 96  
Takes pills very irregularly  
Stops voluntarily treatment on December 20

Therapy begun 27 June 96  
HU          300 mg TID  
ddI          200 mg BID  
INDINAVIR   800 mg TID

| VIRAL LOAD IN THE BLOOD | | | VIRAL LOAD IN THE LYMPH NODE | | | | VIRAL |
|---|---|---|---|---|---|---|---|
| D/M/Y | bDNA/PCR | PCR/RIGHT | D/M/Y | p24 antigen expression | HIV-RNA in situ | HIV DNA PCR | LOAD SEMEN |
| | | | | FDC   Cells | FDC   Cells | | |
| 21.06.96 | 12620 | 80041 | | | | | 07.01.97 |
| 9.7.96 | <500 | 1099 stop (12–19) | 16.10.96 | | | | <400 copies/ml |
| 19.7.96 | 1134 | 5356 rebound | | –     – | –     – | 2 pos. in 44 million | Not detected |
| 19.8.96 | <500 | <200 neg | 01.7.97 | | | | |
| 5.9.96 | <500 | <200 | | –     – | –     – | 3 pos. in 44 million | negative |
| 1.10.96 | <500 | <200 stop 26 Oct | | | | | |
| 29.10.96 | <500 | <200 | | | | | |
| 1.11.96 | | <200 | | | | | |
| 8.11.96 | <400 | 324; <200 starts 11 Nov | | | | | |
| 11.12.96 | <500 | <200; <200 stop 20 Dec | | | | | |
| 07.01.97 | <400 | <200; <200 2.5 wks a. stop | | | | | |
| 16.01.97 | | 279; <200 | | | | | |
| 27.01.97 | <500 | 221; <200 5 wks a. stop | | | | | |
| 7.2.97 | <500 | nd | | | | | |
| 14.2.97 | 700? | nd | | | | | |

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 21.6.96 | 1,408 | 210 | 1,020 | 370 | 26 | 710 | 50 | 0.52 |
| 24.6.96 | 1,411 | 230 | 1,020 | 410 | 29 | 690 | 49 | 0.59 |
| 26.6.96 | 1,965 | 270 | 1,430 | 570 | 29 | 940 | 48 | 0.61 |
| 19.7.96 | 1,643 | 310 | 1,130 | 490 | 30 | 620 | 38 | 0.79 |
| 19.8.96 | 1,880 | 280 | 1,330 | 660 | 35 | 730 | 39 | 0.90 |
| 1.10.96 | 1,587 | 238 | 1,152 | 571 | 36 | 540 | 34 | 1.06 |
| 1.11.96 | 1,907 | 305 | 1,426 | 572 | 30 | 801 | 42 | 0.71 |
| 11.12.96 | 2,304 | 392 | 1,553 | 991 | 43 | 968 | 42 | 1.02 |
| 7.1.97 | 2,145 | 429 | 1,471 | 751 | 35 | 686 | 32 | 1.09 |
| 29.1.97 | 1,961 | 412 | 1,302 | 628 | 32 | 588 | 30 | 1.07 |
| 7.2.97 | 2,306 | 369 | 1,591 | 738 | 32 | 853 | 37 | 0.87 |
| 14.02.97 | 2,232 | 379 | 1,482 | 670 | 30 | 781 | 35 | 0.86 |

SEROCONVERSION BY WESTERN BLOT TEST

| Date | HIV 1 + 2 | gp160 | gp120 | p65 | p55 | gp41/43 | p32 | p24 | p18 |
|---|---|---|---|---|---|---|---|---|---|
| 11.6.96 | ± | – | – | – | – | – | – | – | – |
| 21.6.96 | ± | – | – | – | – | – | – | – | – |
| 26.6.96 | ± | – | – | – | – | – | – | – | – |
| 19.7.96 | + | + | – | – | – | – | – | ± | – |
| 1.10.96 | + | + | – | ± | – | – | + | – | – |
| 8.11.96 | + | + | ± | – | – | – | – | ± | ± |

TABLE 4

VIRAL LOAD AND LYMPHOCYTE ANALYSES OF PATIENT TD

| Infected November 95 | | | Therapy begun 29 July 96 | |
|---|---|---|---|---|
| Seroconverted December 95 | | | HU | 300 mg TID |
| Hepatitis March 96 | | | ddI | 200 mg BID |
| | | | INDINAVIR | 800 mg TID |

| VIRAL LOAD IN THE BLOOD | | | VIRAL LOAD IN THE LYMPH NODE | | | |
|---|---|---|---|---|---|---|
| D/M/Y | bDNA/PCR | PCR/RIGHT | | HIV-RNA in situ | HIV DNA PCR | VIRAL LOAD SEMEN |
| 08.03.96 | 47,940 | | Cells FDC | Cells | | 07.01.97 |
| 13.03.96 | <10,000 | | 07.01.97 | | | <400 copies/ml |
| 25.04.96 | 39,290 | | – – | – | negative | |
| 23.04.96 | 32,980 | | | | | |
| 20.06.96 | 30,090 | | | | | |
| 18.07.96 | 45,290 | | | | | |
| 22.07.96 | 42,000 | | | | | |
| 22.07.96 | 114,000 | | | | | |
| 01.08.96 | 48,000 | | | | | |
| 10.09.96 | 750 | | | | | |
| 21.10.96 | <500 | "neg?" | | | | |
| 04.11.96 | <500 | <200 | | | | |
| 23.12.96 | <500 | <200 | | | | |
| 30.01.97 | <400 | <200 | | | | |

LYMPHOCYTE POPULATION ANALYSIS

| Date D/M/Y | Lymph. | B.Ly | T-Ly | CD4 | CD4 % | CD8 | CD8 % | Ratio |
|---|---|---|---|---|---|---|---|---|
| 25.04.96 | 1745 | 90 | 1140 | 490 | 28 | 1010 | 58 | 0.49 |
| 23.05.96 | 1934 | 120 | 1620 | 620 | 32 | 1120 | 58 | 0.55 |
| 20.06.96 | 1885 | 110 | 1550 | 550 | 29 | 1060 | 56 | 0.52 |
| 18.07.96 | 1649 | 120 | 1340 | 480 | 29 | 970 | 59 | 0.49 |
| 10.09.96 | 2253 | 203 | 1794 | 879 | 39 | 1104 | 49 | 0.80 |
| 23.12.96 | 1560 | 156 | 1213 | 530 | 34 | 640 | 41 | 0.83 |
| 08.01.96 | 2504 | 225 | 2098 | 1102 | 44 | 1102 | 44 | 1.00 |
| 30.01.97 | 2448 | 269 | 1928 | 881 | 36 | 979 | 40 | 0.90 |
| 14.02.97 | 2545 | 204 | 2138 | 1069 | 42 | 1044 | 41 | 1.02 |

TABLE 5

VIRAL LOAD AND LYMPHOCYTE ANALYSES OF PATIENT LF

| Infected May 95? | | | Therapy begun 26 June 96 | |
|---|---|---|---|---|
| Naive (never treated before) | | | HU | 300 mg TID |
| | | | ddI | 200 mg BID |
| | | | INDINAVIR | 800 mg TID |

| VIRAL LOAD IN THE BLOOD | | | VIRAL LOAD IN THE LYMPH NODE D/M/Y | | | |
|---|---|---|---|---|---|---|
| D/M/Y | bDNA/PCR | PCR/RIGHT | p24 antigen expression | HIV-RNA in situ | HIV DNA PCR | VIRAL LOAD SEMEN |
| 05.03.96 | 70,200 | | FDC Cells | FDC Cells | | 07.01.97 |
| 15.03.96 | 40,950 | | 07.01.97 | | | <400 copies/ml |
| 04.04.96 | 14,910 | | – – | – | positive | |
| 10.5.96 | 27,290 | | | | | |
| 07.06.96 | 30,820 | | | | | |
| 12.07.96 | <500 | | | | | |
| 20.08.96 | <500 | | | | | |
| 24.09.96 | <500 | | | | | |
| 10.10.96 | <500 | | | | | |
| 08.11.96 | <400 | | | | | |
| 14.12.96 | <500 | | | | | |
| 7.1.97 | | <200 | | | | |

TABLE 5-continued

VIRAL LOAD AND LYMPHOCYTE ANALYSES OF PATIENT LF

LYMPHOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 06.03.96 | 2880 | 194 | 2095 | 693 | 24 | 1358 | 49 | 0.51 |
| 22.03.96 | 2772 | 168 | 2193 | 729 | 26 | 1374 | 49 | 0.53 |
| 10.05.96 | 3578 | 250 | 2650 | 790 | 22 | 1860 | 52 | 0.42 |
| 07.06.96 | 2756 | 190 | 1930 | 630 | 23 | 1490 | 54 | 0.42 |
| 12.07.96 | 2584 | 260 | 1880 | 750 | 29 | 1190 | 46 | 0.63 |
| 26.08.96 | 2268 | 249 | 1701 | 771 | 34 | 998 | 44 | 0.77 |
| 10.10.96 | 2508 | 201 | 1826 | 853 | 34 | 953 | 38 | 0.90 |
| 04.12.96 | 1888 | 189 | 1385 | 642 | 34 | 680 | 36 | 0.94 |
| 07.01.97 | 2350 | 235 | 1833 | 940 | 40 | 870 | 37 | 1.08 |

TABLE 6

VIRAL LOAD AND LYMPHOCYTE ANALYSES FOR PATENT LJ

Infected 1987 or 1991  Therapy begun 28 March 96  Therapy changed 1 July 96
Naive (never treated before)  HU 300 mg TID  HU 300 mg TID
ddI 200 mg BID  ddI 200 mg BID
RITONAVIR 600 mg BID  INDINAVIR 800 mg TID

| VIRAL LOAD IN THE BLOOD | | VIRAL LOAD IN THE LYMPH NODE | | | | |
|---|---|---|---|---|---|---|
| D/M/Y | PCR/RIGHT | D/M/Y | | | | VIRAL LOAD SEMEN |
| 21.2.96 | | 2.10.96 | size: 6.5 × 12.5 | 2 weeks a. neg | | 07.01.97 |
| 25.3.96 | 95229 | p24 antigen expression | | HIV-RNA in situ | | <400 copies/ml |
| 1.4.96 | | FDC | Cells | FDC | Cells | |
| 23.4.95 | 757 | + | − | − | (few)+ | |
| 7.5.96 | | | | | | |
| 30.5.96 | 836 | | | | | |
| 28.6.96 | 393 | | | | | |
| 22.7.96 | 347 | | | | | |
| 6.8.96 | | | | | | |
| 5.9.96 | | | | | | |
| 19.9.96 | <200 | | | | | |
| 14.10.96 | <200 | | | | | |
| 18.11.96 | | | | | | |
| 4.12.96 | <200 | | | | | |
| 18.12.96 | | | | | | |
| 28.1.97 | <200 | | | | | |

LYMPHOTOCYTE POPULATION ANALYSIS

| D/M/Y | Lymph. | B.Ly | T-Ly | CD4 | CD4 % | CD8 | CD8 % | Ratio |
|---|---|---|---|---|---|---|---|---|
| 09.02.96 | 1,680 | 176 | 1,382 | 303 | 19 | 1,053 | 66 | 0.29 |
| 22.02.96 | 2,178 | 220 | 1,960 | 374 | 17 | 1,560 | 71 | 0.24 |
| 26.03.96 | 1,754 | 190 | 1,490 | 330 | 19 | 1,190 | 68 | 0.28 |
| 01.04.96 | 2,317 | 260 | 2,020 | 420 | 18 | 1,600 | 69 | 0.26 |
| 08.05.96 | 1,946 | 230 | 1,640 | 330 | 17 | 1,380 | 71 | 0.24 |
| 30.05.96 | 2,346 | 230 | 1,970 | 400 | 17 | 1,710 | 73 | 0.23 |
| 22.07.96 | 1,544 | 220 | 1,310 | 340 | 22 | 990 | 64 | 0.34 |
| 23.08.96 | 1,640 | 200 | 1,390 | 360 | 22 | 1,020 | 62 | 0.35 |
| 14.10.96 | 1,830 | 220 | 1,537 | 439 | 24 | 1,061 | 58 | 0.41 |
| 04.12.96 | 1,447 | 130 | 1,270 | 362 | 25 | 897 | 62 | 0.40 |

TABLE 6-continued

VIRAL LOAD AND LYMPHOCYTE ANALYSES FOR PATENT LJ

| 17.01.97 | 1,685 | 185 | 1,445 | 438 | 26 | 1,078 | 64 | 0.41 |
| 28.01.97 | 1,260 | 126 | 1,098 | 290 | 23 | 794 | 63 | 0.37 |

Table Legend:
1. Each table summarizes viral load, lymphocyte and, where applicable, seroconversion analyses for a single patient over time.
2. Dates are listed as day/month/year "D/M/Y".
3. Viral load was measured on the dates indicated by a contract laboratory ("bDNA/PCR") or by the inventor's laboratory ("PCR/RIGHT").
4. Results for tests for viral load in the lymph nodes were recorded as follows:
"p24 antigen expression": measured by antibodies against HIV protein p24 applied to a thin layer of lymnph node tissue.
"HIV-RNA in situ": measured by nucleotide binding to lymph node tissue.
"HIV DNA PCR": standard test for viral load.
"Not detected" means not tested on that date
"FDC": Follicular Dendritic Cells
"Cells": Lymph node cells generally.
5. Lymphocyte population analysis shows the complement of the patient's lymphocytes at the given dates.
"Lymph.": Total number of lymphocytes.
"B.Ly": Total number of B-lymphocytes.
"T-Ly": Total number of T-Lymphocytes.
"CD4" Total number of CD4+ lymphocytes.
"CD4 %": The percentage of total lymphocytes that are CD4+ lymphocytes.
"CD8": Total number of CD8+ lymphocytes.
"CD8 %": The percentage of total lymphocytes that are CD8+ lymphocytes.
"Ratio": The CD4+/CD8+ ratio.
Seroconversion was shown by Western Blot analysis. The patient's blood was screened for antibodies to the listed HIV proteins at the given dates.

What is claimed is:

1. A method of treating HIV infection in human beings, comprising the steps of:
    testing the blood for viral load;
    if the viral load is above about 5 log copies per mL, administering a drug combination consisting of hydroxyurea, ddI and Indinavir; until the viral load is reduced to below about 500 copies per mL; if the viral load is below about 5 log copies per ml,
    administering a drug combination consisting of hydroxyurea and ddI.

2. A method of treating HIV infection in human beings where the patient is failing one or more therapies other than the drug combination consisting of hydroxyurea, ddI and Indinavir, comprising the steps of:
    testing blood for viral load; if the viral load is above about 5 log copies per mL administering a drug combination consisting of hydroxyurea, ddI and Indinavir, until the viral load is reduced to below about 500 copies per mL;
    if the viral load is below about 5 log copies per ml, administering a drug combination consisting of hydroxyurea and ddI.

* * * * *